(12) United States Patent
Navakatikyan

(10) Patent No.: US 9,173,610 B2
(45) Date of Patent: Nov. 3, 2015

(54) EEG SEIZURE ANALYSIS

(75) Inventor: Michael Alexander Navakatikyan, Auckland (NZ)

(73) Assignee: Natus Medical Incorporated, San Carlos, CA (US)

( * ) Notice: Subject to any disclaimer, the term of this patent is extended or adjusted under 35 U.S.C. 154(b) by 3056 days.

(21) Appl. No.: 10/569,535

(22) PCT Filed: Aug. 23, 2004

(86) PCT No.: PCT/NZ2004/000198
§ 371 (c)(1),
(2), (4) Date: May 28, 2008

(87) PCT Pub. No.: WO2005/018448
PCT Pub. Date: Mar. 3, 2005

(65) Prior Publication Data
US 2008/0228100 A1  Sep. 18, 2008

(30) Foreign Application Priority Data
Aug. 22, 2003 (NZ) ........................................ 527751

(51) Int. Cl.
*A61B 5/02* (2006.01)
*A61B 5/00* (2006.01)
*A61B 5/0476* (2006.01)

(52) U.S. Cl.
CPC ............ *A61B 5/4094* (2013.01); *A61B 5/0476* (2013.01); *A61B 5/7282* (2013.01); *A61B 5/7435* (2013.01)

(58) Field of Classification Search
CPC ........................... A61B 5/0476; A61B 5/0482
USPC ................................................ 600/544–545
See application file for complete search history.

(56) References Cited

U.S. PATENT DOCUMENTS 5,311,876 A * 5/1994 Olsen et al. ................... 600/544
6,406,427 B1   6/2002 Williams et al.
(Continued)

FOREIGN PATENT DOCUMENTS

WO    WO02071936 A1    9/2002

OTHER PUBLICATIONS

"Cortical and Subcortical Correlates of Electroencephalographic Alpha Rhythm Modulation", Feige et al., Journal of Neurophysiology, 93, 2864-2872, 2005.*

(Continued)

*Primary Examiner* — Patricia Mallari
*Assistant Examiner* — Vasuda Ramachandran
(74) *Attorney, Agent, or Firm* — Temmerman Law Office; Mathew J. Temmerman

(57) ABSTRACT

Automated seizure detection from within an electroencephalogram (EEG) by instrumental means employs novel algorithms within software, using specific measurements of individual waves in trains, rather than any "bulk" process. The acquired signal is filtered, the wave shapes are individually described within a number of parallel runs using a variety of parameters, then criteria (including regularity criteria) are calculated and applied in order to create raw detection results. Finally the raw results are "integrated" for display. As a result, reported seizures closely follow the incidence and duration of seizures detected by trained clinicians. The invention is useful in intensive-care monitoring of EEGs from neonates and in EEG monitoring in general.

52 Claims, 6 Drawing Sheets

(56) References Cited

U.S. PATENT DOCUMENTS

| | | | |
|---|---|---|---|
| 6,442,421 B1* | 8/2002 | Le Van Quyen et al. | 600/544 |
| 6,622,036 B1* | 9/2003 | Suffin | 600/544 |
| 2003/0083716 A1* | 5/2003 | Nicolelis et al. | 607/45 |

OTHER PUBLICATIONS

"A Time-Frequency Approach for Newborn Seizure Detection" by Boashash et al., IEEE Engineering in Medicine and Biology, Sep./Oct. 2001, pp. 54-64.*

Liu A et al: "Detection of neonatal seizures through computerized EEG analysis" Electroencephalography and Clinical Neurophysiology, Elsevier, vol. 82, No. 1, Jan. 1, 1992, pp. 30-37.

Gotman J et al: "Automatic seizure detection in the newborn: methods and initial evaluation" Electroencephalography and Clinical Neurophysiology, Elsevier, vol. 103, No. 3, Sep. 1, 1997, pp. 356-362.

Boashash B et al: "A time-frequency approach for newborn seizure detection." IEEE Engineering in Medicine and Biology Magazine : The Quarterly Magazine of the Engineering in Medicine & Biology Society, Sep.-Oct. 2001, vol. 20, No. 5, Sep. 2001, pp. 54-64.

Navakatikyan, M.A.; Barrett, C.J.; Head, G.A.; Ricketts, J.H.; Malpas, S.C., "A real-time algorithm for the quantification of blood pressure waveforms," Biomedical Engineering, IEEE Transactions on , vol. 49, No. 7, pp. 662,670, Jul. 2002.

* cited by examiner

EEG SEIZURE ANALYSIS

CROSS-REFERENCE TO OTHER APPLICATIONS

This is a National Phase of International Application No. PCT/NZ2004/000198, filed on Aug. 23, 2004, which claims priority from New Zealand Patent Application No. 527751, filed on Aug. 22, 2003.

TECHNICAL FIELD

This invention relates to biophysical data collection and analysis; to electroencephalography; to EEG waveform analysis, and in particular to instrumental means for EEG seizure detection by software within on-line or off-line surveillance; over short or long periods.

BACKGROUND ART

Electroencephalography signals are often analysed and reviewed in order to make sense of, and/or to condense the copious amount of data collected from the brain of a subject under study. Techniques include many frequency-based derivatives such as the fast Fourier transform, counts of zero crossings, spectral analysis, spectral edge, intensity, and the like.

The applicant is the assignee of patent applications and patents such as U.S. Pat. No. 6,406,427 relating to a brain monitoring device first intended for use with premature near-term human infants many of whom suffer brain trauma near the time of delivery. Monitoring can lead to appropriate treatments and to a better indication of outcome.

However, in a hospital's Intensive Care Unit (ICU), it is also necessary to be able to monitor brain seizures in term infants through to adults. In this environment, patients are often paralyzed or unconscious and seizures are silent and can not currently be reliably observed or monitored. Often, only significant/severe seizures need be detected but detection needs to be carried out with a very high degree of reliability in order to be able to assist busy non-expert staff in the ICU.

Further applications of the device include the monitoring of anaesthesia and brain function during and after procedures such as open-heart surgery in which micro-emboli lodging within end-arteries are not uncommon.

The pathology of brain damage includes a primary and a secondary response at least part of which is endogenous damage, as exhibited by neurones. Sometimes seizures, which may lack correlated clinical signs perhaps because of administered drugs, form part of the response pattern. A seizure involves the synchronous firing of a large number of neurones, which is abnormal. A resulting waveform may comprise a distinctive regular series of waves ranging from very sharp "spikes" to "sine-like waves" originating from firing by many neurones in unison within the field under study, although in a pre-term infant, especially if already under treatment, or if the damage site is small or localised, the waveforms may be relatively small and difficult to recognise.

One reason to seek the recognition of seizure waveforms is that if they can then be inhibited or suppressed by drugs or other treatment the outcome for the patient is usually improved.

There is a need for an automatic form of seizure detection by instrumental means (usually operating within a brain monitoring device), so that continuous, reliable, and immediate reporting of the onset or existence of a seizure is provided. It would be an advantage to be able to provide a very reliable severe seizure monitor suitable for use in an Intensive Care Unit of a hospital.

WO02071936A and the article entitled "A real-time algorithm for the qualification of blood pressure waveforms" published in IEEE Transactions on Biomedical Engineering Vol. 49, No. 7. July 2002 disclose a real time algorithm for the quantification of biological oscillatory signals such as arterial blood pressure. The algorithm analyses the original signal by determining certain parameters so that false peaks (which are typical of arterial blood pressure signals) can be removed to accurately quantify heartbeats.

It is therefore an object of this invention to provide real-time seizure detection by instrumental means (that is, without human analysis) which will go at least some way towards meeting the above requirements or which will at least to provide the industry with a useful choice.

DISCLOSURE OF INVENTION

Accordingly, in a first aspect the invention consists in a method of detecting seizures in an electroencephalogram (EEG) signal comprising the steps of:
i) obtaining representative numerical data characterising the waveform shape of the EEG signal at a plurality of times within the EEG signal,
ii) carrying out a calculation or calculations on at least some of the representative numerical data to produce related numerical data at a plurality of times within the EEG signal,
iii) comparing the related numerical data at at least some of said plurality of times to predetermined criteria, and
iv) determining that a seizure event has taken place at a particular time or times in the EEG signal if the comparison at that time or times indicates that the related data is within the predetermined criteria.

Preferably, the EEG signal is comprised of multiple separate channels and the method is carried out on each channel individually and the individual results combined together.

Preferably, the method also includes the steps of:
v) analysing the length of time between adjacent positive determinations of a seizure event, and
vi) determining that a seizure event has taken place within said period of time if said length of time is less than a predetermined minimum time value.

Preferably, said step of obtaining representative numerical data comprises determining the positions of local peaks and troughs within the EEG signal.

Preferably, said step of obtaining representative numerical data comprises the steps of:
a) averaging or low-pass filtering the EEG signal to obtain an averaged EEG signal,
b) comparing the EEG signal to the averaged EEG signal to locate intersection positions where the EEG signal intersects with the averaged EEG signal,
c) for each pair of first and subsequent intersection points, determining the location of each peak (or trough) of the EEG signal and, for each pair of subsequent intersection point and its subsequent intersection point, determining the location of each trough (or peak) of the EEG signal, and
d) recording the position of each trough, subsequent peak and two corresponding intersection points in respective data groups.

Preferably, a comparison is made between the amount of time between adjacent peaks and a predetermined refractory time period and if the time between adjacent peaks is less than the refractory time period then the later occurring of the adjacent peaks is disregarded.

Preferably, if a plurality of peaks of the EEG signal are recorded within said refractory time period then all but the maximum of those peaks are disregarded.

Preferably, the averaged EEG signal is determined by a moving average calculation based upon a predetermined time window of the EEG signal and wherein the step of obtaining representative numerical data is repeated a plurality of times with different time window and refractory time period values and the individual results combined.

Preferably, step of obtaining representative numerical data is carried out on the EEG signal and also on an inverted version of the EEG signal and the results combined.

Preferably, the step of carrying out a calculation or calculations on at least some of the representative numerical data includes determining the amplitude of the peak and trough in each data group with respect to a predetermined base level and associating the determined amplitude with its respective group.

Preferably, the base level for determining amplitude is a line connecting the troughs either side of said peak and the base level for determining trough amplitude is a line connecting the peaks either side of said trough.

Preferably, the step of carrying out a calculation or calculations on at least some of the representative numerical data includes determining the time interval between the peak and/or trough and/or one or both intersection points from a first data group with their corresponding respective peak and/or trough and/or one or both intersection points from a subsequent data group and associating the determined time interval or intervals with one of the data groups.

Preferably, for each pair of adjacent data groups, the determined amplitudes are compared to obtain said related numerical data in the form of a numerical indication of the similarity of the amplitude of the adjacent data groups and/or one or more of the respective determined time interval differences are compared to obtain said related numerical data in the form of a numerical indication of the similarity of the intervals of the adjacent data groups.

Preferably, numerical values indicative of amplitude and interval difference are combined in predetermined ratios to provide said predetermined criteria.

Preferably, the numerical values indicative of amplitude and interval difference are combined in a plurality of different ratios in order to produce multiple separate criteria as said predetermined criteria.

Preferably, a determination that a seizure event has taken place is made only if the related data remains within the predetermined criteria for a predetermined number of adjacent data groups.

Preferably, said related numerical data also includes data representative of the change in shape of the EEG signal as described by a predetermined number of serially adjacent data groups.

Preferably, each point in said averaged EEG signal is shifted upwards by a predetermined amount prior to the step of comparing the EEG signal to the averaged EEG signal.

Preferably, a seizure event will not be determined for times within the EEG signal where the amplitude or average amplitude of a predetermined number of serially adjacent peaks or a predetermined number of serially adjacent troughs is less than a predetermined threshold.

Preferably, noise introduced into the EEG signal by external electrical and/or mechanical equipment is detected and a seizure event will not be determined to have occurred during periods of time in which the determined noise exceeds a predetermined threshold.

Preferably, one of the different time window and refractory time period value combinations detects noise added to the EEG signal by external electrical and/or mechanical equipment.

Preferably, said EEG signal is first divided into segments of a predetermined length and each segment is analysed separately.

Preferably, the EEG signal undergoes analogue to digital conversion and is then band-pass filtered prior to said step of obtaining representative numerical data characterising the waveform.

Preferably, said method includes the further step of:
comparing the shapes of adjacent portions of the EEG signal to obtain related numerical data indicative of the variability of the shape of the EEG signal from portion to portion,
wherein a seizure event will not be determined to have occurred for times within the EEG signal where the related numerical data indicative of the variability of the shape of the EEG signal does not meet predetermined variability criteria.

Preferably, the related numerical data includes the linear coefficient of correlation between adjacent portions of the EEG signal.

Preferably, the method includes the further step of:
analysing the shape of a selected portion or portions of the EEG signal to obtain related numerical data indicative of the shape of the selected portion or respective portions of the EEG signal,
wherein a seizure event will not be determined to have occurred for times within the EEG signal where the related numerical data indicative of the shape of the selected portion or portions of the EEG signal does not meet predetermined shape criteria.

Preferably, the portion of the EEG signal is between adjacent peaks in the EEG signal and the predetermined shape criteria include a requirement that each portion of the EEG waveform must include a central dip in amplitude.

In a second aspect, the invention consists in a computer program which when executed causes a computer to carry out the method according to the first aspect.

In a third aspect, the invention consists in a computer readable medium on which the computer program according to the second aspect is stored.

In a fourth aspect, the invention consists in a device for detecting seizures in an electroencephalogram (EEG) signal comprising:
means for receiving an EEG signal, and
control means programmed to carry out the method according to the first aspect on the received EEG signal.

In a fifth aspect, the invention consists in a device for detecting seizures in an electroencephalogram (EEG) signal comprising:
means for obtaining representative numerical data characterising the waveform shape of the EEG signal at a plurality of times within the EEG signal,
means for carrying out a calculation or calculations on at least some of the representative numerical data to produce related numerical data at a plurality of times within the EEG signal,
means for comparing the related numerical data at at least some of said plurality of times to predetermined criteria, and means for determining that a seizure event has taken place at a particular time or times in the EEG signal if the comparison at that time or times indicates that the related data is within the predetermined criteria.

Preferably, wherein the EEG signal is comprised of multiple separate channels and the means for obtaining representative numerical data obtains representative numerical data on each channel individually and the individual results produced by the means for determining that a seizure event has taken are combined together.

Preferably, the device also comprises:
means for analysing the length of time between adjacent positive determinations of a seizure event, and
means for determining that a seizure event has taken place within said period of time if said length of time is less than a predetermined minimum time value.

Preferably, said means for obtaining representative numerical data determines the positions of local peaks and troughs within the EEG signal.

Preferably, said means for obtaining representative numerical data:
a) averages or low-pass filters the EEG signal to obtain an averaged EEG signal,
b) compares the EEG signal to the averaged EEG signal to locate intersection positions where the EEG signal intersects with the averaged EEG signal,
c) for each pair of first and subsequent intersection points, determines the location of each peak (or trough) of the EEG signal and, for each pair of subsequent and its subsequent intersection point, determines the location of each trough (or peak) of the EEG signal, and
d) records the position of each trough, subsequent peak and two corresponding intersection points in respective data groups.

Preferably, a comparison is made between the amount of time between adjacent peaks and a predetermined refractory time period and if the time between adjacent peaks is less than the refractory time period then the later occurring of the adjacent peaks is disregarded.

Preferably, if a plurality of peaks of the EEG signal are recorded within said refractory time period then all but the maximum of those peaks are disregarded.

Preferably, the averaged EEG signal is determined by a moving average calculation based upon a predetermined time window of the EEG signal and wherein the means for obtaining representative numerical data from the EEG signal obtains a plurality of sets of representative data, each with different time window and refractory time period values, and the individual sets are combined.

Preferably, the means for obtaining representative numerical data obtains said numerical data from the EEG signal and also from an inverted version of the EEG signal and the results are combined.

Preferably, the means for carrying out a calculation or calculations on at least some of the representative numerical data determines the amplitude of the peak and trough in each data group with respect to a predetermined base level and associates the determined amplitude with its respective group.

Preferably, the base level for determining amplitude is a line connecting the troughs either side of said peak and the base level for determining trough amplitude is a line connecting the peaks either side of said trough.

Preferably, the means for carrying out a calculation or calculations on at least some of the representative numerical data determines the time interval between the peak and/or trough and/or one or both intersection points from a first data group with their corresponding respective peak and/or trough and/or one or both intersection points from a subsequent data group and associates the determined time interval or intervals with one of the data groups.

Preferably, for each pair of adjacent data groups, the determined amplitudes are compared to obtain said related numerical data in the form of a numerical indication of the similarity of the amplitude of the adjacent data groups and/or one or more of the respective determined time interval differences are compared to obtain said related numerical data in the form of a numerical indication of the similarity of the intervals of the adjacent data groups.

Preferably, numerical values indicative of amplitude and interval difference are combined in predetermined ratios to provide said predetermined criteria.

Preferably, the numerical values indicative of amplitude and interval difference are combined in a plurality of different ratios in order to produce multiple separate criteria as said predetermined criteria.

Preferably, a determination is made that a seizure event has taken place only if the related data remains within the predetermined criteria for a predetermined number of adjacent data groups.

Preferably, said related numerical data also includes data representative of the change in shape of the EEG signal as described by a predetermined number of serially adjacent data groups.

Preferably, each point in said averaged EEG signal is shifted upwards by a predetermined amount prior to the step of comparing the EEG signal to the averaged EEG signal.

Preferably, a seizure event will not be determined for times within the EEG signal where the amplitude or average amplitude of a predetermined number of serially adjacent peaks or a predetermined number of serially adjacent troughs is less than a predetermined threshold.

Preferably, noise introduced into the EEG signal by external electrical and/or mechanical equipment is detected and a seizure event will not be determined to have occurred during periods of time in which the determined noise exceeds a predetermined threshold.

Preferably, one of the different time window and refractory time period value combinations detects noise added to the EEG signal by external electrical and/or mechanical equipment.

Preferably, said EEG signal is first divided into segments of a predetermined length and each segment is analysed separately.

Preferably, the EEG signal undergoes analogue to digital conversion and is then band-pass filtered prior to said means for obtaining representative numerical data characterising the waveform.

Preferably, said device further comprises:
means for comparing the shapes of adjacent portions of the EEG signal to obtain related numerical data indicative of the variability of the shape of the EEG signal from portion to portion,
wherein a seizure event will not be determined to have occurred for times within the EEG signal where the related numerical data indicative of the variability of the shape of the EEG signal does not meet predetermined variability criteria.

Preferably, the related numerical data includes the linear coefficient of correlation between adjacent portions of the EEG signal.

Preferably, the device further comprises:
means for analysing the shape of a selected portion or portions of the EEG signal to obtain related numerical data indicative of the shape of the selected portion or respective portions of the EEG signal, wherein a seizure event will not be determined to have occurred for times within the EEG signal where the related numerical data indicative of the shape of the selected portion or portions of the EEG signal does not meet predetermined shape criteria.

Preferably, the portion of the EEG signal is between adjacent peaks in the EEG signal and the predetermined shape criteria include a requirement that each portion of the EEG waveform must include a central dip in amplitude.

In a further aspect, the invention consists in a method for automatic seizure detection from electroencephalograph (EEG) signals, the method comprising analysis of collected data and reduction of the data into sets of individual wave descriptors, followed by analysis thereof.

Preferably an individual wave is considered in context of adjacent and nearby waves.

Preferably the analysis develops a criterion describing any wave train in terms of timing with amplitude regularity.

Preferably the analysis also develops a criterion describing any wave train in terms of timing regularity.

Preferably results are assessed in terms of whether the criteria currently are above, or below a threshold value.

Preferably the analysis applies a series of test conditions to the incoming data and analyses the data in terms of each condition at the same time.

A first test condition relates to a selected averaging time intervals (ATI) used which preferably lies in the range of from 50 mS to 3000 mS, and preferably a range of ATIs are processed together as a group.

A second test relates to the sign (normal or inverse) applied to the incoming data and preferably both signs are processed together, for each ATI.

A third test condition is an ATI intended to emphasise artefacts introduced by external electrical and/or mechanical equipment and preferably an "identification of seizure" state is blocked in the event of likely artefact interference.

Supplementary test conditions apply a range of constants to the data during analysis, including an exclusion interval or "refractory period", an offset applied to raised moving averages, and wave shape analysis criteria.

Preferably an "identification of seizure" state is entered by the method for automatic seizure detection if, at any time, any one of a plurality of decisions made on any one of (a) any ATI, (b) any polarity, under a preferred set of constants indicates the presence of a seizure.

Preferably the "identification of seizure" state is blocked in the event of either the detected amplitude decreasing below a predetermined limit, or in the event of any interference or artefact noise being detected.

Preferably the "identification of seizure" state is confirmed in the event of the state continuing for at least a predetermined period and an example procedure applies a moving window 60 sec long to the duration of an identified seizure in 4 sec intervals, using a threshold of 0.35 of the maximum length per 4 seconds, then closing gaps (that is, converting the non-seizure intervals between adjacent identified seizures into identified seizures if the gaps are less than 2 sec, or 25% of the adjacent identified seizure durations, but not if the gaps are longer than 15 seconds; and then discarding any identified seizures with durations shorter than about 10 seconds.

Preferably the analysis is capable of being carried out in real time or substantially so.

Preferably the analysis is carried out by software operating within a dedicated instrument capable of use for clinical purposes: surveillance of EEG signals and reporting on seizures and on other parameters.

Optionally the software may be used within a general-purpose digital computer.

In a second broad aspect this invention provides a method for automatic seizure detection including the steps of:

(1) accepting at least one channel of EEG signals from a source, (2) converting the channel into digitised form, (3) applying filtering transformations to the incoming signals, (4) applying a waveform analysis procedure including (a) wave detection, (b) calculation and application of criteria based on the detected waves, and (c) integrating relevant criteria, (5) detecting signals likely to conform to the expected configuration of seizure-like signals, (6) and reporting the detection of a seizure to a person, (7) so that continuous, reliable, and immediate reporting of the presence of a seizure is provided.

Preferably the source is directly from one or more electrodes applied to an animal's cranium.

Optionally the source is indirectly connected to an animal's cranium; through a telecommunications link and/or a data storage device.

Preferably the filtering transformations applied to the incoming signals include a band-pass filter.

Optionally, the filtering transformations applied to the incoming signals include one or more procedures capable of removing artefacts from the signals or at least to detect and exclude said artefacts from the incoming signals.

Preferably the signals are collected as an indefinite series of separate blocks each comprising a plurality of waves, and blocks lasting for two second (2000 mS) epochs are preferred.

Preferably a moving average is constructed, and preferably the moving average is applied over at least one averaging time interval (ATI) in the range of from 50 mS to 3000 mS (note that analysis can pass seamlessly between one block and the next).

Preferably, three points are located and quantified for each wave having a peak or maximum: the before-peak intersection (Bpi) of the wave with the moving average, the after-peak intersection (Api) of the wave with the moving average, and the position of the peak.

Preferably a trough or minimum point for the waveform preceding the Bpi and following the previous Api is located.

Optionally, the moving average may include a constant value based on a proportion of the difference between peak and trough.

Preferably, an exclusion interval is applied following a recognised peak so that a following wave, if occurring within the refractory period, is not included within calculations.

Preferably a procedure for determining the most appropriate peak is one that selects the highest of several neighbouring peaks, within an epoch comparable to a refractory period.

Preferably a procedure is applied in order to repeat the procedure described previously in this section upon the inverse of the wave to be analysed, either by inverting the wave or by inverting the polarity of "peak" and "valley" and "raised" and like terms.

Preferably a numerical description of each wave, as obtained by a procedure as previously described in this section, includes a Bpi, an Api, a trough, and a peak.

Preferably also the numerical description includes the interval from the previous peak to the present peak, and includes the interval from the previous trough to the present trough.

Optionally the procedure described above is repeated with varied time settings.

In a third broad aspect the invention is used in co-operation with other EEG collection and analysis software within a machine dedicated to the monitoring of the status of a brain of a patient under treatment.

Preferably the output of the invention is capable of being displayed and recorded together with other outputs describing other characteristics of the EEG so that a more complete clinical description of the brain of the patient under treatment is provided.

Preferably the machine can be controlled by a user so that the raw EEG data giving rise to reported seizures may be reviewed at a later time, and preferably any detected seizures within that data are highlighted.

BRIEF DESCRIPTION OF THE DRAWINGS

The description of the invention to be provided herein is given purely by way of example and is not to be taken in any way as limiting the scope or extent of the invention.

BEST MODES FOR CARRYING OUT THE INVENTION

Example 1

Figure 1:
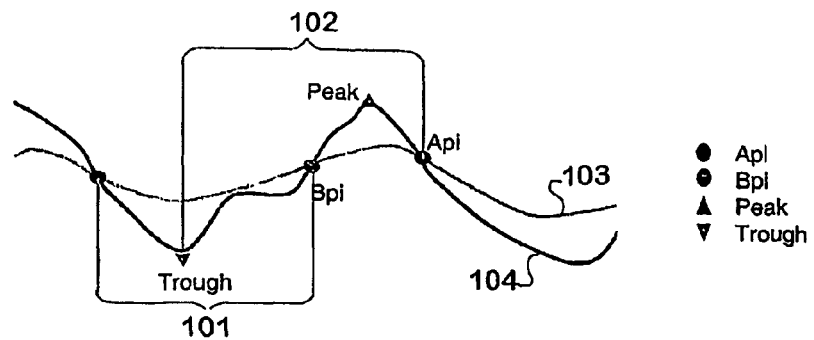
FIG. 1 is a diagram showing detection of the wave critical points (step 1).

In the intended application, electroencephalogram (EEG) waveforms are analysed during a procedure of long-term collection from usually a single set of electrodes during monitoring of the brain of an endangered patient, for example a near term infant, or an older patient during or after surgery. The procedure could be applied to multiple electrode recordings.

The main objective of the invention is to automatically and accurately detect regularity in the EEG signal, which is assumed to represent seizure activity. In summary, there are three major steps as follows:

1) breaking of the EEG signal (one or many channels) into "waves" and measuring different characteristics of the individual waves belonging to three mutually exclusive and exhaustive categories: length, amplitude and shape.

2) carrying out parallel processing of calculations on the waves with different detection parameters in order to analyse waves with differing ranges of frequencies (and length).

3) calculating the similarity of consecutive waves in the each of parallel processing lines, and if regularity in the categories (all, or some of them) exceeds some threshold then a primary seizure-like activity is considered to have been discovered.

4) a final part of detection includes the assessment (integration) of consecutive and parallel primary seizure-like activities to decide whether an actual seizure is detected.

The preferred method begins with numerical analysis of waveform shapes in order to detect characteristic patterns of waveforms indicating seizures. At least one channel of EEG signals from the brain of a person under close/intensive care are supplied for analysis. The channel is filtered (low-pass or more preferably band-pass) in order to retain frequencies above about 0.2 Hz and below about 15 or more preferably about 25 Hz. Waveforms are digitised at a sampling frequency of 64 or more preferably 128 or 256 Hz. A numerical process to be described below calculates and applies criteria based on the detected waveforms, then further criteria are applied in order to detect any seizure patterns during the monitored period. Although characteristic seizure patterns can be recognised, the patient's condition and co-existing treatments may make these harder to recognise. The instrument in which this analysis is used Is intended to reliably and continuously emulate the skills of a clinician over a long period and to report the detection of a seizure, in real-time, to a caregiver.

Preferably the signals are received for analysis as an indefinite series of separate blocks of typically two seconds of EEG signals from at least one channel (pair of electrodes). Blocks or "epochs" lasting for two seconds are preferred. As shown in Table 1 or in FIG. 11, data is processed (regardless of the above block structure) using a series of averaging time intervals (ATI) in the example range of from 50 mS to 3000 mS. A group of ATIs are processed concurrently. In order to increase the chance of correct detection occurring, the inverse original EEG signal may also be processed in parallel, with all algorithm steps applied to it also. This may be particularly useful if the EEG signal is significantly asymmetrical.

1. Wave Detection

Initial Critical Points.

A moving average corresponding to each epoch is constructed and used to compensate for slow changes in mean signal value. The moving average may be replaced by any appropriate mechanism which effectively averages or low-pass filters the EEG signal. Referring to FIG. 1, a process for finding the initial critical points of detected waves of the incoming EEG signal is applied. This process identifies all the Api (after-peak intersections) and all the Bpi (before-peak intersections) in the data, as being those points where the moving average 103 intersects the filtered EEG signal 104. A "wave" as herein used may be defined as a cluster of critical points identifying a portion of the original EEG signal. For example, a wave may be defined between a first Api and the following Api, from a first to a following Bpi, from a first to a following peak or from a first to a following trough. A process 101 searches for the minimum value (trough) between an Api and a following Bpi, then another process 102 locates the maximum value (peak) between a trough and a following Api. All identified points are stored for later use. In this data reduction procedure, the waves making up the EEG are reduced to a small set of meaningful numbers such as times within the original (recorded) EEG signal.

Refractory Period, and Absolute Maxima.

Figure 2A:
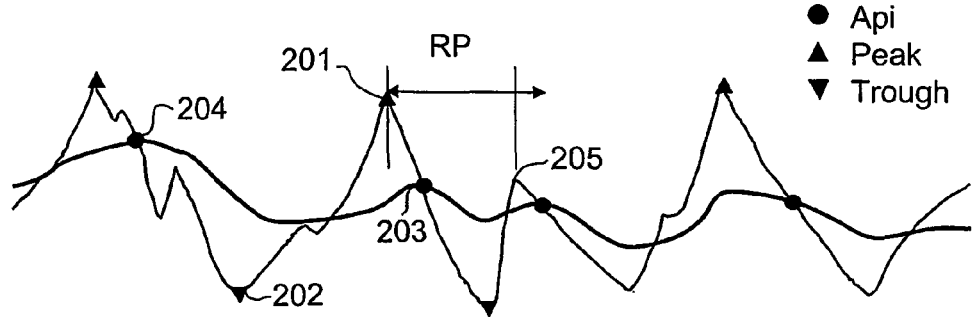
FIGS. 2*a* & 2*b* are diagrams showing how the refractory period is applied and the absolute maximum is determined.
Figure 2B:
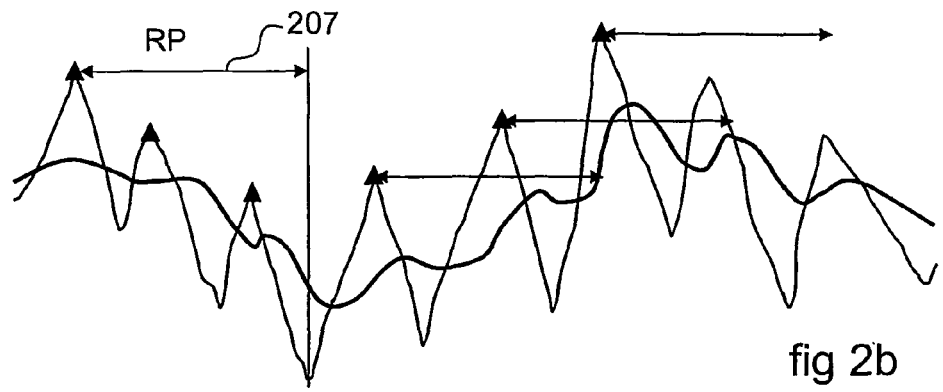

Referring to FIG. 2a, peaks are not allowed to follow more closely than the refractory period (a constant) permits (we use a variety of RPs in our calculations—see Table 1 below). Within a closely spaced group, the true peak is defined as the highest (maximum). It can be seen in FIG. 2a that peak 205 follows peak 201 but that peak 205 is within the refractory period (RP) and therefore peak 205 is discarded and peak 201 established as a true peak. Once a true peak 201 is established, the related (preceding) trough 202, Api 203 and Bpi 204 are associated with it as a set (or cluster). An additional requirement is that within a RP, the true peak is the absolute maximum (see FIG. 2b) and so an initially selected peak may be disregarded and replaced by a closely following, larger peak. In FIG. 2b, individual refractory periods 207 are overlapping other waves.

Rejection of Small Events—Pulse Threshold Factor.

Figure 3:
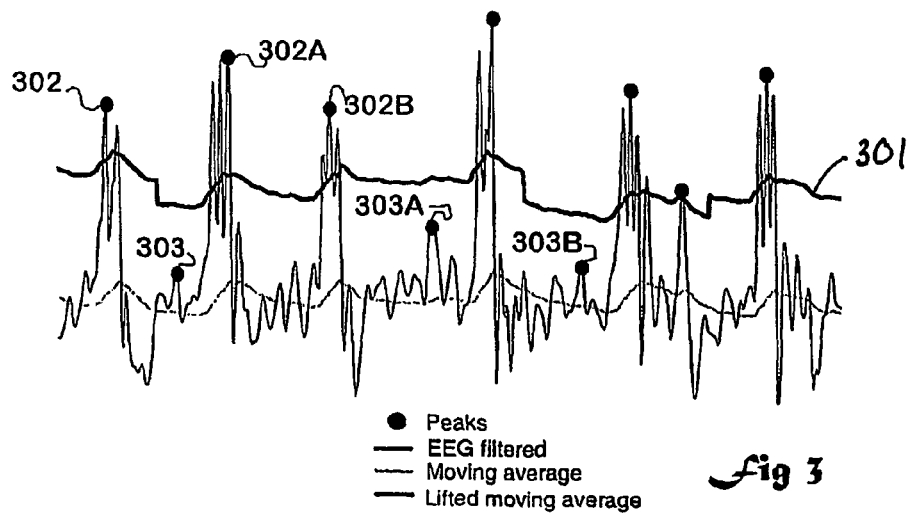
FIG. 3 is a diagram showing how the pulse threshold fraction is applied—involving a lifted moving average.
Figure 4:
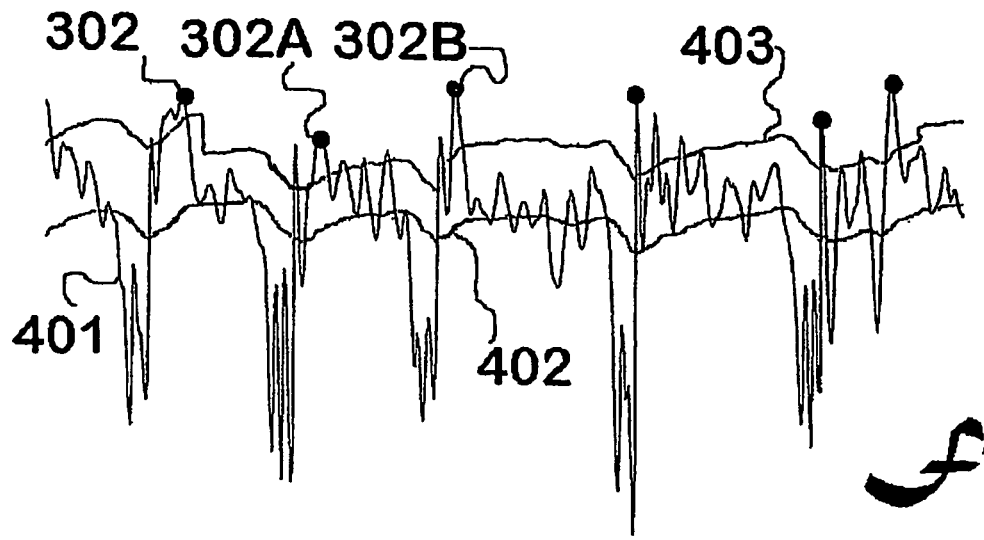
FIG. 4 is a diagram showing how the inverse signal is also processed.

One approach is to lift the moving average such as by a constant amount or perhaps an adaptive constant amount (depending on recent history of relative peak/trough amplitudes—the pulse threshold fraction of Table 1) or by a fraction of the distance between maximum and average in an epoch and process only those peaks that have a value greater than the momentary value of the lifted moving average. Referring to FIG. 3, the lifted moving average 301 demarcates seizure-like peaks (302, 302A, 302B) from peaks more or less buried within general EEG activity (such as 303, 303A, and 303B). In case the polarity of the input wave is inverted, according to which electrode is closer to the site involved for example, this inherently asymmetric process should be repeated on the inverse of the data. FIG. 4 shows an inverted input wave 401, a moving average 402, a lifted moving average 403, and detected points 302, 302A, 302B.

Quantification of Recognised Events.

Figure 5A:
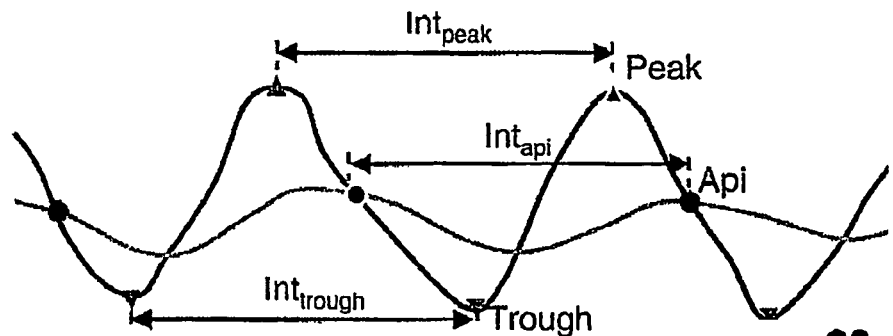
FIGS. 5*a* & 5*b* are diagrams showing determination of timing and amplitudes in relation to the wave critical points.
Figure 5B:
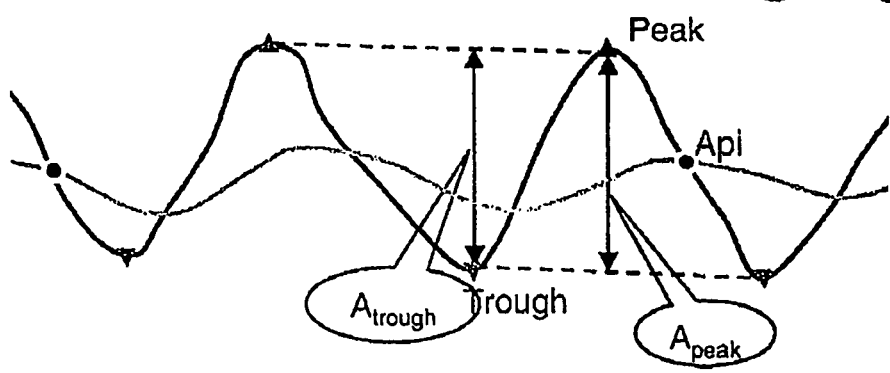

Each wave has four critical points as previously mentioned: peak, trough, Api and Bpi, which are recorded. In addition, the time elapsed between any such point and the following point of the same type (such as peak to peak time, trough to trough time, and the like) are recorded. Furthermore, the amplitudes of peaks (relative to a baseline between preceding and succeeding troughs) and troughs (relative to a baseline between preceding and succeeding peaks) are recorded. Similar amplitude recordings for Api and Bpi could be made. These measurements are shown in FIG. 5a and FIG. 5b.

Parallel Processing of Variety of Parameters.

Preferably, in order to cater for various eventualities such as different wave frequencies and polarities, a number of EEG signal samples of varying ATI durations undergo analysis effectively simultaneously. In this example an additional "run" is also made in order to pick up the dominant frequency of artefacts caused by a ventilator to which the patient is ordinarily connected. See Table 1; also the left hand side of FIG. 11. For each of the, for example, six runs, both normal and inverse analyses, locating peaks, troughs, Api's and Bpi's are carried out, and processed through the criteria Crit 1 and Crit2 (see below).

TABLE 1

Example. Characteristics of parallel processing runs of the algorithm.

| Run | ATI length (ms) | RP (ms) | Pulse threshold Fraction of distance between maximum and average in an epoch |
|---|---|---|---|
| 0 (for external device freq detection | 50 | 25 | 0 |
| 1 | 100 | 50 | 0 |
| 2 | 300 | 150 | 0.5 |
| 3 | 700 | 450 | 0.5 |
| 4 | 1000 | 500 | 0.5 |
| 5 | 3000 | 1500 | 0 |

2. Calculation of Criteria and Application.

Min/Max Ratios.

For each successive pair of critical points, the ratios of minimum interval to maximum interval, and minimum amplitude to maximum amplitude are calculated. Other values are derived as shown: Formulas used:

$$I_r = \min(\text{Interval})/\max(\text{Interval}) \quad (1)$$

$$A_r = \min(\text{Amplitude})/\max(\text{Amplitude}) \quad (2)$$

$$\text{Crit1} = I_r \times (A_r)^{1/2} \quad (3)$$

$$\text{Crit2} = I_r \times (A_r)^{1/150} \quad (4)$$

$$\text{Seizure1: Crit1} > 0.8, N=4, N^*=1 \quad (5)$$

$$\text{Seizure2: Crit2} > 0.85, N=4, N^*=4 \quad (6)$$

The $A_r$ (amplitude ratio) calculations can be carried out on peak amplitudes, trough amplitudes or an average of both. The $I_r$ (interval ratio) calculations can be carried out on trough, peak, Api or Bpi, intervals or a combination of any two or more of these intervals. $I_r$ and $A_r$ are assumed to tend towards 1 as the signals analysed become more like seizures.

Crit1 and Crit2 are combinations of $I_r$ and $A_r$; in Crit1 the $A_r$ influence is diminished compared to $I_r$, while in Crit2 the influence of $A_r$ is almost negated and so Crit2 is applied to detection of time regularity on its own rather than to combined time-amplitude regularity. At this stage of development, we calculate an average Crit1 for four successive $I_r$'s and $A_r$'s (N=4) and take the value of 0.8 as the threshold for determining that a seizure wave (more strictly, a seizure-like event) is present. Formula (5) assesses the regularity of 6 successive peaks/troughs/Apis. Crit2 is also calculated for four successive $I_r$'s and $A_r$'s but in this case we consider that the seizure-like event is detected if Crit2 is over 0.85 four successive times (formula 6). This criterion has assessed the regularity of 9 successive sets of peaks/troughs/Apis (presently Bpi is not used in the above calculations but it could be incorporated).

Reverting to the process used to determine seizure, Crit 1 and Crit 2 as previously described function as logical variables associated with Api position in time and assigned to the time interval from the previous to the present Api. In this Example, the 24 or 30 versions arising from analysis (see FIG. 11 and Table 1) are passed though a 24/30-input "OR" decision-making process which is capable of counting the number of initial seizure recognition inputs. The output of that process is "ANDed" in another decision-making process with both an amplitude test in which signals must be over 5 microvolts (see below) and a ventilator noise test (see below). The output of the AND decision-making process is an output logical variable herein termed "Total primary events". The process described in FIG. 11 is for a single channel of the EEG signal and is repeated on each EEG channel and the results logically ORed together to produce a primary detection output 1006 shown in FIG. 10.

Figure 10:
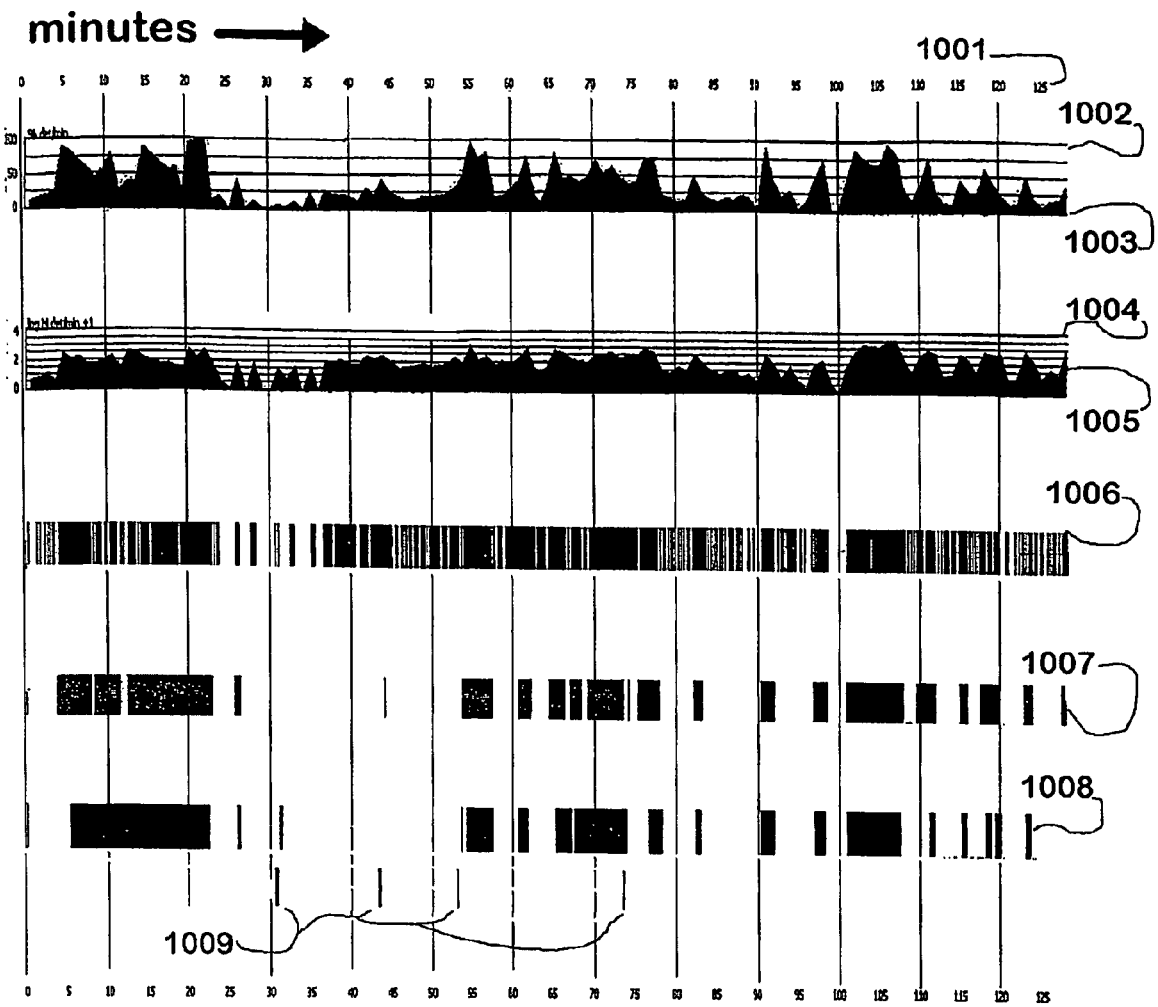
FIG. 10 is a diagram showing detection of seizures by the system against time, including primary total detections, then integrated detections, as compared with a human interpretation of the waves, and an indication of errors.
Figure 11:
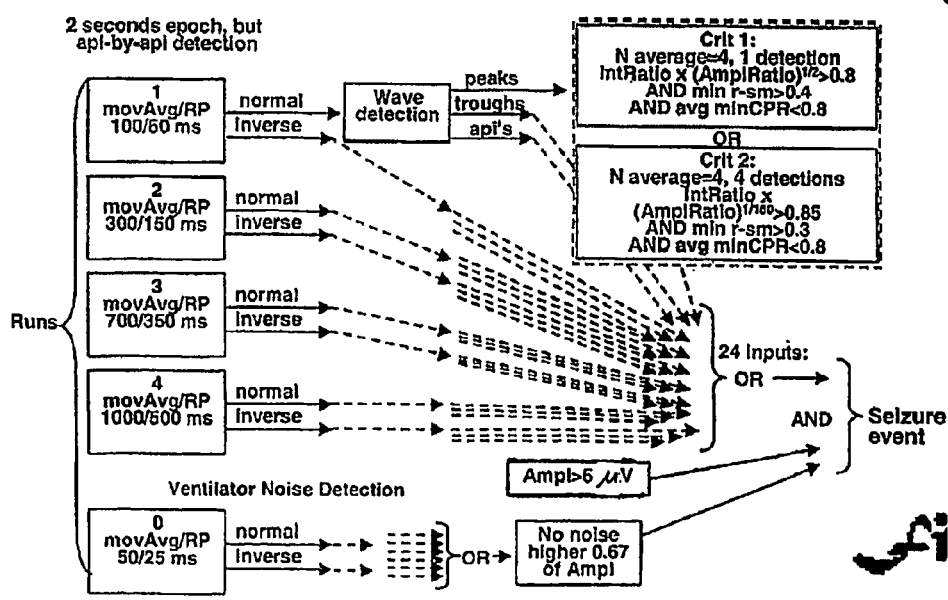
FIG. 11 is a diagram showing data flow during application of the algorithm.

FIG. 11 shows an overview of the algorithm; the boxes at left correspond to the left column in Table 1 (note that the numbers are different; this shows flexibility of the invention). The criteria are shown in the boxes at top right. The 24-30 input OR decision-making process and the 3-input AND decision-making process, also amplitude, and ventilator noise detection, are shown. The term "Seizure event" corresponds to the "primary total detections" line of bars 1006 in FIG. 10. A variety of methods can be used separately or in combination to regularise this output. These methods include: closing gaps shorter than a predetermined duration, accepting only events longer than a predetermined duration, taking the median of the seizure lengths within a short ATI (such as 4 seconds), taking the 25% ranking value of the seizure lengths within a short ATI (such as 4 seconds), calculating a moving rectangular window average, and calculating a moving exponentially forgetting window average.

Figure 6A:
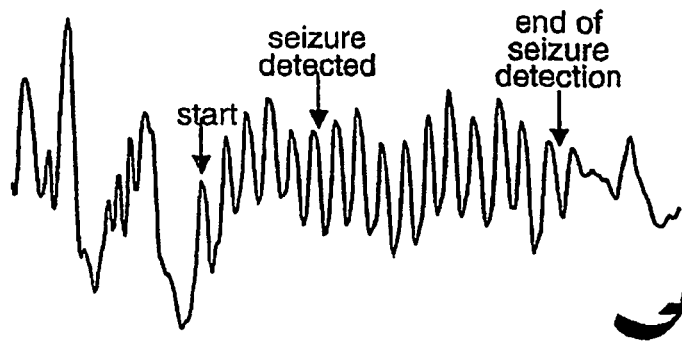
FIGS. 6*a* & 6*b* are diagrams showing detection of seizures by criterion "Crit 1">0.8, applied to peaks. The upper trace is an EEG signal. The lower trace shows evaluation of Crit 1 in relation to the signal, using Interval ratio, Amplitude ratio, and a combination (Crit 1). The threshold of 0.8 is a dotted line.
Figure 6B:
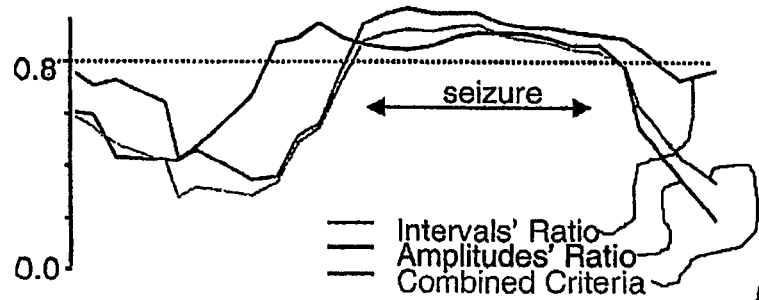

FIG. 6a (an input EEG signal after filtering, including seizure waves) and 6b (detected criteria) comprise a diagram in which evaluation of Crit 1 is carried out in relation to the signal, using Interval ratio, Amplitude ratio, and their combination (Crit 1). The threshold of 0.8 is a dotted line. The curve for Combined Criteria (Crit 1) rises above 0.8 a little while after the point labelled "start" showing detection of seizures.

Figure 7A:
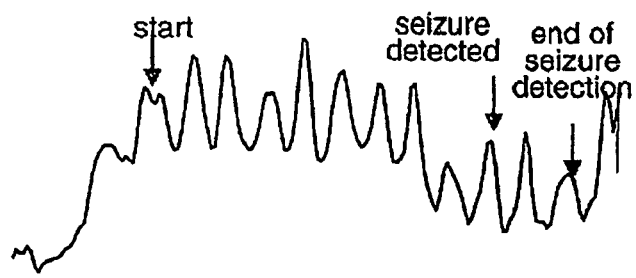
FIGS. 7*a* & 7*b* are diagrams showing detection of seizures by criterion "Crit 2", applied to troughs. The threshold of 0.85 is a dotted line. The upper trace is another EEG signal. The lower trace shows evaluation of Crit 1 in relation to the signal, using Interval ratio, Amplitude ratio, and a combination of both Crit 1 and Crit 2.
Figure 7B:
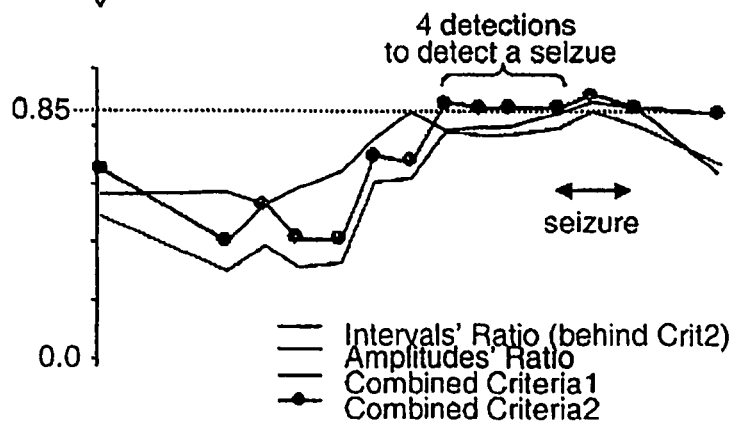

In FIG. 7a the trace is another EEG signal diagram showing detection of seizures by Crit 2, applied to troughs. The threshold of 0.85 is shown as a dotted line. The lower trace shows evaluation of Crit 1 in relation to the signal, using Interval ratio, Amplitude ratio, and a combination of both Crit 1 and Crit 2 (dots on line). Note also that four detections were required in order to define a seizure, hence the time when a seizure is reported occurred later.

Criteria of Variability for the Wave Shape.

Figure 8:
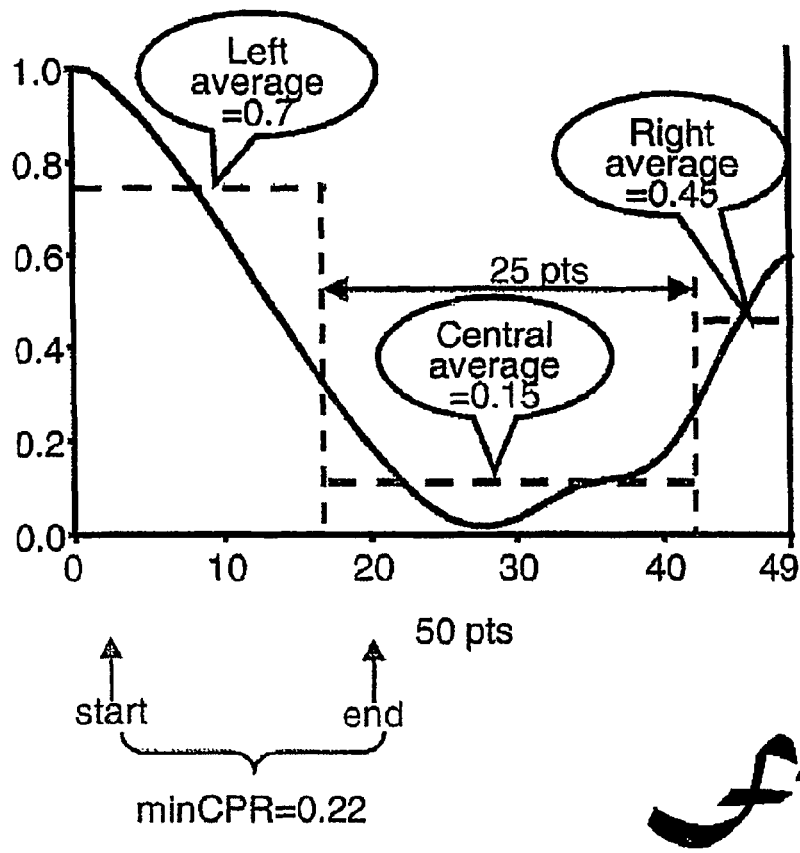
FIG. 8 is a diagram that shows generation of another criterion (the parameter "minCPR") to assess the acceptance of wave shape for further evaluation.
Figure 9:
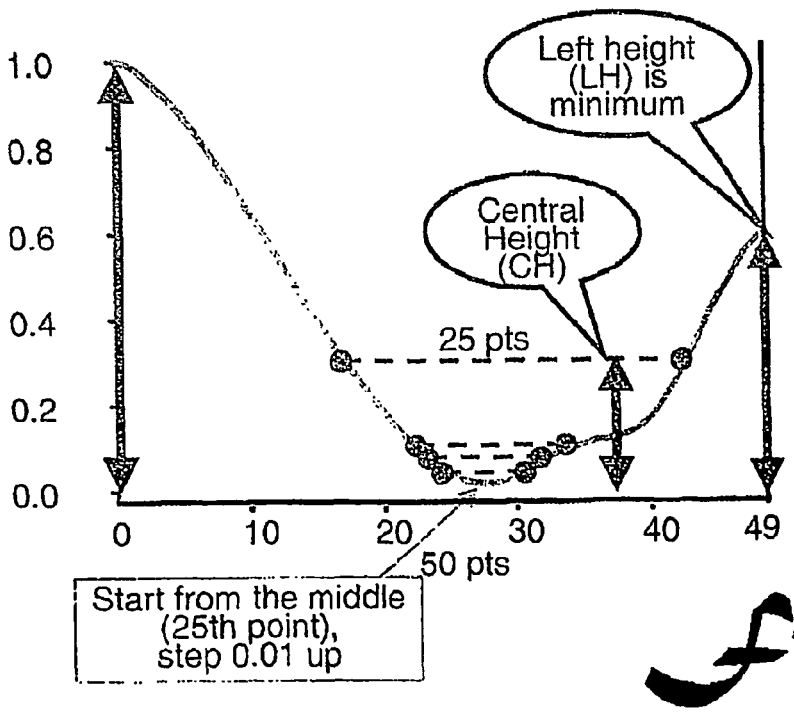
FIG. 9 is a diagram that shows generation of yet another criterion (the "fill-in criterion") to also ascertain whether the shape of the wave is acceptable for use in evaluation of seizure detection

FIGS. 8 and 9 show further methods which may be used to detect the presence of trains of similar shaped waves as a sign of a seizure.

The first criterion is based upon the assumption that the waves in a train should have a similar shape thus the linear coefficient of correlation between a wave and a following wave is calculated in terms of sets of critical points as previously described (for example, between peaks, between troughs, and between Apis). We presently believe that the Bpis are less useful in this respect. Alternatively, any other analytical technique for providing a measure of the similarity could be used, such as rank coefficient of correlation or ANOVA (Analysis Of Variance).

Each wave's (in this instance "wave" preferably describes that portion of the EEG signal between two adjacent peaks or two adjacent troughs) amplitude is scaled to lie within a constant range (0 to 1) and by duration to encompass 50 data points (see FIG. 8). Each wave is then smoothed by a 7-point moving average procedure and the coefficient of linear correlation (r) calculated between successive pairs of waves. An example criterion for presence of a seizure-like event is that at least 4 consecutive values for r exceed 0.4.

As mentioned above, FIG. 8 shows a wave, scaled to 0-1 amplitude and 50 points duration. 25 points from the middle of the wave are taken, and amplitude averages of the signal in the left, right, and central portions are computed (0.7, 0.45, and 0.15 respectively in the example of FIG. 8). The "central power ratio" or CPR is the ratio of the central average to the lesser of the two other averages (0.15/0.45=0.33 in this illustration). This calculation is repeated 15 times, starting at point 5 (as if it was the left side of the central portion) then at point 6 and completing the series of calculations at point 20. The parameter "minCPR" is the lowest CPR obtained from this data set. This parameter is saved for use elsewhere. This criteria for the application of the internal and amplitude criteria is average minCPR<0.8.

FIG. 9 depicts another criterion to assess whether the wave is acceptable for further processing and inclusion in the seizure determination decision and shows another wave, scaled in amplitude to between 0-1 and in duration to 50 points. The algorithm starts at point 25 and measures a horizontal line across the trough of the wave. The algorithm raises the starting point by $1/100$ units, and repeats the procedure until the length measured is 25 points. Then the algorithm calculates the ratio between the current measuring height (central height at which width of wave=25 pts) and the height of the lower wave shape boundary that is at either 0 or 50 pts. This ratio is termed the "fill-in criterion" and we have found that this test works better on smaller regular waves than does the minCPR test described in relation to FIG. 8. basically, this criterion ensures that only waves with a central minimum (that is, a dip in their middle portion) are included in processing for seizure detection. For example, for the wave shown in FIGS. 8 and 9, the minCPR result is too big and thereby falsely indicates that the wave does not have a central trough whereas the fill-in criterion result indicates a central trough.

Additional absolute amplitude criterion. In order to reject apparent seizures of altogether too low an amplitude, and assuming that a train of four waves has been obtained, the relevant rejection procedure takes the average amplitude of the peaks, and the average amplitude of the troughs and selects the minimum of them—min AvgAmpl. This value is compared to an absolute threshold—currently set at 5 microvolts. If the value is less, the train is disregarded (see box "Ampl>5 uV" in FIG. 11) by setting all amplitude and interval ratios to zero which effectively suppresses the seizure detection at this point.

Noise suppression.

In order to reject artefacts introduced by electromagnetic noise produced by external electrical and/or mechanical equipment such as by ventilator activity (which for pre-term babies includes a vibratory component), one set of normal and inverse wave processing is carried out with a 50 mS ATI, and a refractory period RP of 25 mS. (lower left; FIG. 11). Waves of a regular and known frequency (for example, the ventilator frequency is usually manually set by a healthcare professional attending the patient) are detected through measurement of intervals between critical points, derived as described previously. The average of two intervals is examined for peaks, troughs, and APIs and waves at about the ventilator frequency are taken to be an artefact. Further, average noise amplitude is derived from average amplitude of peaks and troughs. The algorithm multiplies these by the threshold fraction (tF) which is a constant, for example 1.5, and the resulting parameter "MaxNoiseAmplxtF" is compared with the previously obtained parameter minAvgAmpl. The test for presence of unacceptable levels of artefactual noise of ventilator origin is: Occurs at the time points of Api, and if "MaxNoiseAmplxtF" is greater than minAvgAmpl, and if the frequency is in the right range, then for either of normal and inverse waves, the test is positive. In that case, any apparent seizures detected within other channels are blocked.

3. Integrating Criteria (Global Seizure Criteria)

FIG. 10 illustrates typical performance of the process in accordance with the invention with an example set of real data (the example data shown is actually the serial combination of six separate data sets). The time scale (horizontal 1001) extends from 0 (at left) to 125 minutes. The first set of bars 1006 shows the primary total detections, that is, the output of the process illustrated in FIG. 11. The curves towards the top of FIG. 10 illustrate (1003) the time covered by detected seizures per minute expressed as a percentage on a linear amplitude scale 1002 (from all channels from ATI variants), and then on a logarithmic amplitude scale 1004, the number of logical positive detections per minute is displayed as curve 1005. Graph 1007 shows integrated detections (determined as described below), for comparison with an independently identified occurrence series 1008 (as determined by an expert clinician).

In the example shown in FIG. 11, "integrated detections" refers to the results of a procedure in which, for example, a moving window 60 sec long is applied to the duration of seizure in 4 sec intervals. A threshold is set at 0.35 of the maximum length per 4 seconds. Time intervals where the duration of seizures per 4 s is above the threshold are considered to be "global" seizures. Further processes can close gaps (non-seizure intervals between adjacent global seizures) if they are less than, for example 2 sec, or 25% of the adjacent global seizures' duration (maximum length of gap allowed to discard=about 15 sec) and then in a further process any global seizure shorter than about 10 seconds may be discarded. This combination resulted in bar graph 1007—integrated detections. Bars 1009 reveal four differences from the expert clinician verdicts were revealed as shown in the lowest bar 1008; one missed seizure, one false positive, another missed seizure and another false positive. Note that the total duration of errors arising from the invention is low (2 sec of false positives in this example of 125 minutes).

There are a variety of ways in which the primary total detections 1006 can be converted to integrated detections 1007, such as:
 i) closing gaps shorter than some predefined length,
 ii) selecting elementary events shorter than some predefined length,
 iii) taking the median of the seizure length per short period of time (for example, seconds),
 iv) taking 25% ranking value of the seizure length per short period of time (for example, 4 seconds),
 v) calculating a moving rectangular window average, and/or
 vi) calculating a moving exponentially forgetting average.

The whole procedure is preferably implemented in software and carried out in real time, using any appropriate programming environment such as LABVIEW™ manufactured by National Instruments, Austin, Tex., USA (at least during development), C or derivatives such as C++, Java, or in assembler, as is appropriate for technical requirements, and as is known in the art.

Example 2

The procedures described above have been implemented by integrating with existing software within the "Brain Rescue Monitor" (BRM) device made by the applicant. This device runs software to display and record parameters such as spectral edge, intensity (2-20 Hz) and amplitude of incoming or stored EEG waveforms. The BRM implementation is preferably used in combination with signal quality measures to ensure reliability. These signal quality measures may include some or all of the following:
 1) sufficiently low contact impedance (<about 10 kΩ),
 2) appropriate amplitude range,
 3) absence of high frequency/EMG interference,
 4) absence of electrode artefacts,
 5) absence of motion artefacts,
 6) absence of amplifier errors,
 7) absence of ECG artefact.

Figure 12:
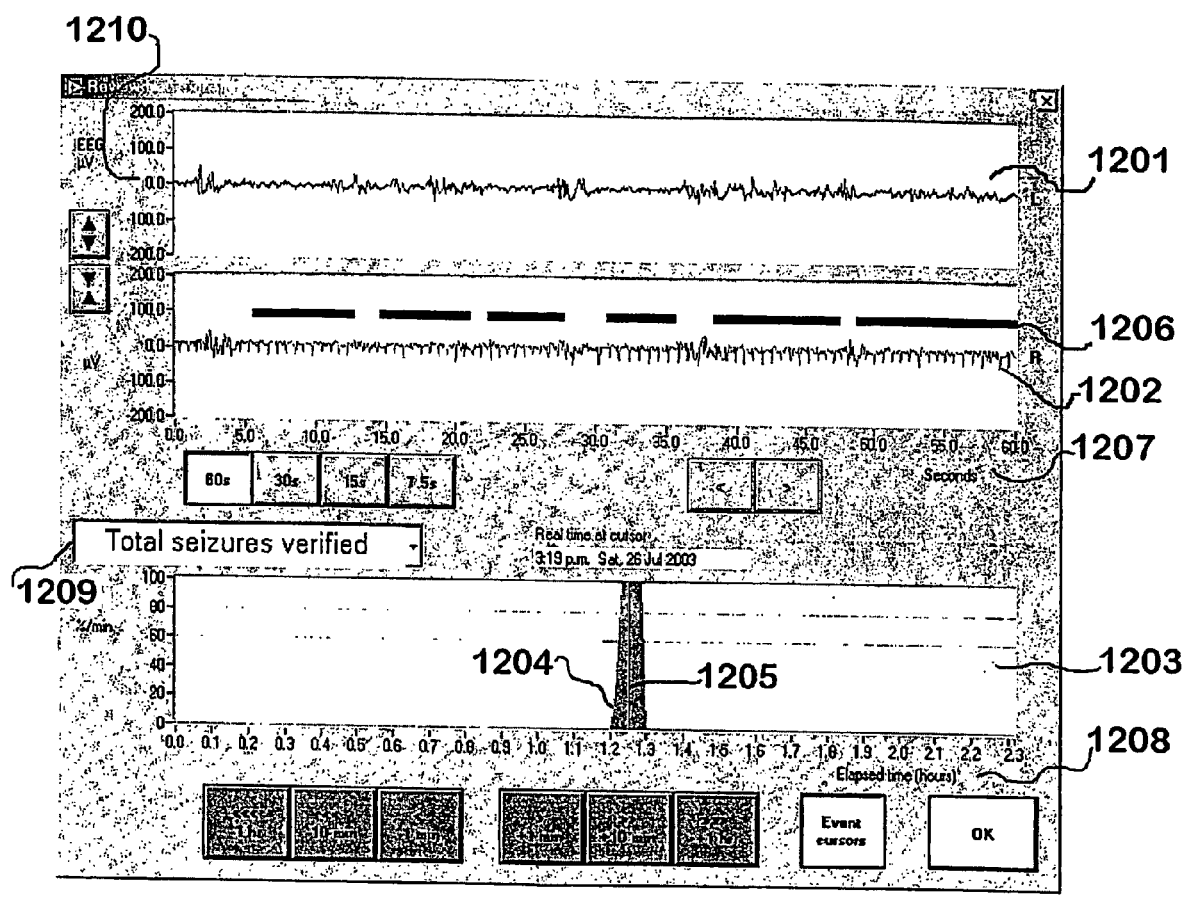
FIG. 12 is a screen capture shot from a brain monitoring device that uses the algorithm to detect, record, and display seizures in a clinical application; the screen showing EEG data including seizures during a "data recall" mode of operation.

The implementation was successful. FIG. 12 illustrates the facility of recall provided by the entire instrument; the lowest panel 1203 of this screen capture image taken from the user's display panel shows a period within a 2.3 hour data collection procedure (see time scale 1208), during which total seizures were verified (profile of hits, 1204, and user's selection of panel data indicated by 1209).

The two upper screens 1201 and 1202 show the recalled original waves from the left and right channels (displayed over a 1 minute period as indicated by time scale 1207) from which the seizures were extracted. Note that black bars 1206 have been drawn over the captured image in order to indicate the waves recognised (in the right side trace only) by the software according to this invention as seizures. Originally the detected seizure waves were indicated in a different colour (red). The position in time of the recalled and displayed waveforms is shown by the user-controllable vertical bar 1205 within the bottom panel 1203 (this is a facility of use to clinicians who may wish to verify the appearance of the detected seizure, given that some types are less serious than others) Scale 1210 is in microvolts for the recalled EEG waveforms.

In this environment we note for example that:
 (a) the invention is capable of detecting relatively small seizures that might not be noticed by eye. They may be small by virtue of involving only a small volume of the brain, by being relatively remote from the recording electrodes, or as a result of the effect of existing medication.
 (b) There is for example a class of minor seizures known as "PLED" (periodic lateralised epileptiform seizures) which are currently believed to be of little or no clinical significance either in terms of an indication for treatment requirements or in reflecting possible outcomes. The invention is being adapted in order to detect the periodic recurrence of such seizures in order to determine their relevance to clinical applications, taking advantage of the long-term monitoring facility provided by the invention. Sometimes PLED seizures precede major seizures.
 (c) Rather than being limited solely to use in real-time, "bedside" applications, this equipment might be used from time to time on a previously recorded set of EEG signals. The display of FIG. 12 was generated within a standard lap-top PC running a simulation of the clinical instrument based on files of real data recorded previously.

Variations

It will be realised that numerical test procedures of this type, applied to biological signals, involve a varying amount of predetermined constants and processes such as the "integrated detections" and the "raised moving average" as described previously. Some of these variables may have been optimised in response to the characteristics of EEG signals from a particular population of patients, such as neonatal infants. In this invention, the reliance on original collection of critical points forms one contrast with prior-art methods such as FFT or others that take the data in bulk. In time, it may become apparent that other values for the selected constants, other constants, and other combinations of ATI duration, block (epoch) duration and refractory period for example are more appropriate either in general or for particular kinds of patient or particular kinds of clinical syndromes. For example, it may be that fewer runs—less variety of simultaneous sampling conditions (see column 1, Table 1) are sufficient.

Optionally, the filtering transformations applied to the incoming signals may include one or more procedures capable of removing artefacts from the signals or at least capable of detecting and excluding artefacts from the incoming signals.

Of course the procedure may be applied to indirectly acquired signals, such as signals collected, optionally stored in a storage device, and telemetered or otherwise communicated to the device running the software which implements this invention from a source, which may be in spatial and/or temporal proximity.

In relation to the procedures leading up to a determination of "seizure present", we can carry out an integration on the single (one of 24, 30 . . . ) channel first, then join them with a form of "OR" function. Integration can be carried out with different levels of certainty—such as larger sensitivity for a general overview, and more conservatively for a treatment alarm.

The software has been shown to work within a brain monitoring machine. It may be installed within any electroencephalograph, which typically has a large number of input channels, as a backup for human analysis of plotted waves from typically up to an hour's use. It may be used as part of a program for determining the appropriate drug treatment for a person prone to epileptiform seizures where its sensitivity over the prior-art assessment of numbers of actual seizures is an advantage.

Further Improvements

We believe that further improvement in the accuracy of the seizure detection system described above may be made by one or more of the following enhancements:

1. Altering the Crit1 and Crit2 seizure detection criteria to include not only minimum amplitude and interval considerations but also average amplitude and interval. Alternatively, we may alter the Crit1 and Crit2 calculations to only take into account peaks (both normal and inverse) and not troughs or Apis. The Crit1 and Crit2 values may also be calculated using the primary values of intervals and/or amplitudes rather than their ratios to avoid a single out of order interval (or amplitude) damaging two consecutive ratios.

2. Improving shape regularity analysis whereby wave shape recognition is carried out and adjacent waves are examined for change in shape to thereby aid in detecting whether seizures are occurring or continuing. This is already carried out by calculating the coefficient of correlation, but could be improved by, for example, altering the seizure detection criteria dependent upon the shape of waves detected. For example, spike-like waves could have different seizure detection criteria than sine-like waves. The wave shape recognition procedure could also be used to identify waveshapes with potential clinical importance, for example spikes, spike-waves etc.

3. Including within the seizure detection criterion an analysis of change in amplitude of the waves.

4. Double directed time scaling for the wave shapes analysis consisting of first obtaining the projection of a first wave in a second wave and the projection of the second wave in the first wave. The data obtained is then combined for shape analysis to obtain exactly paired wave shapes. That is, a) both waves are scaled along Y-axes into the range 0-1 as before; b) both waves are scaled along time axes between 0 and 1 as before; c) in order to have equal numbers of time points in both wave shapes the values of wave 1 are interpolated for the time points of wave 2 and added to wave 1 while the values of wave 2 are interpolated for the time points of wave 1 and added to wave 2; d) the resulting waves are then smoothed as before (although this is not essential), and; e) the coefficient of correlation is calculated.

5. The degree of interruption caused by a detected seizure may be considered by the integrating criteria. For example, if in one minute there are 15 occurrences of primary detected seizures each of 2 seconds duration or 2 occurrences of 15 seconds duration each, then the total duration of the seizure events is the same but it is preferred to minimise the number of interruptions that occur in the detected seizures and this may be accounted for in the integration criteria.

6. Add an uninterrupted interval (for example, 10 seconds) aspect to the seizure detection criteria. That is, we may not only assess the integrated seizures, which are required to have at least 21 seconds of primary seizures per minute to be detected (0.35 of 1 minute), but if a primary seizure is long enough (for example, 10 seconds) then it might be considered as a final (integrated) seizure.

7. A "level of certainty" assessment may be determined for each seizure episode determined by the invention. The "level of certainty" could be a percentage calculated based, for example, upon the amount that the Crit1 and/or Crit2 criteria are exceeded. The "level of certainty" assessment could also or alternatively be simplified by being represented by for example "low", "medium" or "high".

8. Artefact rejection on the basis of electrode impedance or high frequency could be incorporated into the algorithm to reduce false positive seizure detections.

9. An ECG (electrocardiogram) signal showing the patient's heart rate and rhythm could be incorporated into the algorithm as a means to determine artefacts in the EEG signal for rejection.

10. Artefacts at a particular frequency introduced by the operation of external electrical and/or mechanical equipment such as a ventilator may be detected and disregarded. For example, if there is a suspicion that something in the environment, for example a pump, around the patient is causing a regular artefact in the EEG signal and its frequency is known then the algorithm can detect and disregard this frequency.

11. Hyper synchronisation (that is, an excessive level of regularity in the interval, amplitude or shape) may also be used as a criteria for detecting external artefacts. There is a suspicion that external sources of noise or perhaps even ECG (or even ECG superimposed upon the EEG signal), which are regular, are more regular than an EEG seizure wave. Accordingly, the criteria for seizure can have not only a lower boundary (for example, 0.8) but also a higher boundary (for example, 0.95 or 0.98) thereby isolating likely artificially created artefacts.

12. The pulse threshold fraction (see FIGS. 3 and 4) may be made to last for more than one (for example two) iterations. Alternatively, the pulse threshold fraction may be set to zero to remove it from the calculations however it has been found that it may be an important feature because even with larger averaging constants and RP, the running mean reduces quickly and false peaks are detected.

13. Seizure algorithms specifically for ICU use. (that is, for detecting severe more prolonged seizures) may be produced by adapting the invention previously described. This would be achieved by combining the periodic waveform detection with timing/continuity criteria to detect severe seizures greater than about 10-20 seconds overall duration. This would avoid detection of spurious or less important short seizures (such as PLED seizures). The minimum duration of seizures could usefully be about 5 seconds through to about 1 minute.

This software is operational within even an existing computer-based instrument used for monitoring brain activity. Such instruments, such as the Brain Monitor made by the applicant, already display brain activity on a screen and would otherwise rely on a human observer, or a crude system for spotting seizures, to raise an alarm to get the patient further medicated with anti-seizure treatments, because seizure activity can be intrinsically damaging to the brain.

Accuracy appears to be closely similar to that of an experienced clinician.

If the accuracy is found to be satisfactory, automated infusion of an anti-seizure drug may be carried out as a result of detected seizures that rise over a predetermined frequency of occurrence. This is compatible with a "just-enough treatment" regime.

The invention can be included within existing devices, as referred to in this specification. Here, the invention can provide a warning system to alert others to the presence of seizures. The invention can operate continuously over the extended periods (24-96 hours or more) that equipment of this type is normally used, and it does not change its thresholds or judgement over time (a risk with human operators).

Finally, it will be understood that the scope of this invention as described and/or illustrated herein is not limited to the specified embodiments. Those of skill in the art will appreciate that various modifications, additions, known equivalents, and substitutions are possible without departing from the scope and spirit of the invention as set forth.

The invention claimed is:

1. A method of detecting seizures in an electroencephalogram (EEG) signal comprising the steps of:
   i) generating an EEG signal from a set of electrodes applied to an animal's cranium and obtaining an inverted version of the EEG signal;
   ii) obtaining representative numerical data from the EEG signal, wherein the representative numerical data is obtained by comparing the EEG signal to an averaged EEG signal to locate intersection positions to determine the location of each peak or trough of the EEG signal and recording the position of each trough, subsequent peak and two corresponding intersection points in respective data groups, wherein obtaining representative numerical data is carried out on the inverted version of the EEG signal, and the representative numerical data from both the EEG signal and inverted version of the EEG signal are combined;
   iii) characterizing the waveform shape of the EEG signal at a plurality of times within the EEG signal;
   iv) carrying out at least one calculation on at least some of the representative numerical data to produce related numerical data indicative of at least two individual oscillations identified within the EEG signal;
   v) comparing the related numerical data indicative of at least two individual oscillations identified to a predetermined criteria; and
   vi) determining that a seizure event has taken place at a particular time or times in the EEG signal if the related numerical data indicative of at least two individual oscillations identified at said particular time or times in the EEG signal are within the predetermined criteria; wherein a computer is configured to perform the steps i)-vi) above.

2. The method of detecting seizures as claimed in claim 1, wherein the EEG signal comprises multiple separate channels and the method is carried out on each channel individually and the individual results are combined together.

3. The method of detecting seizures as claimed in claim 1, further comprising the steps of:
   i) determining the length of time between adjacent positive determinations of a seizure event, and
   ii) determining that a seizure event has taken place within said length of time if said length of time is less than a predetermined minimum time value.

4. The method of detecting seizures as claimed in claim 1, wherein said step of obtaining representative numerical data comprises determining the positions of local peaks and troughs within the EEG signal.

5. The method of detecting seizures as claimed in claim 4, wherein said step of obtaining representative numerical data comprises the steps of:
   a) averaging or low-pass filtering the EEG signal to obtain the averaged EEG signal;
   b) comparing the EEG signal to the averaged EEG signal to locate intersection positions where the EEG signal intersects with the averaged EEG signal;
   c) for each pair of first and subsequent intersection points, determining the location of each peak or trough of the EEG signal and, for each pair of subsequent and its subsequent intersection point, determining the location of each trough or peak of the EEG signal; and
   d) recording the position of each trough, subsequent peak and two corresponding intersection points in respective data groups.

6. The method of detecting seizures as claimed in claim 5, wherein a comparison is made between the amount of time between adjacent peaks and a predetermined refractory time period, and if the time between adjacent peaks is less than the refractory time period, the later occurring of the adjacent peaks is disregarded.

7. The method of detecting seizures as claimed in claim 6, wherein if a plurality of peaks of the EEG signal are recorded within said refractory time period, all but the maximum of those peaks are disregarded.

8. The method of detecting seizures as claimed in claim 6, wherein the averaged EEG signal is determined by a moving average calculation based upon a predetermined time window of the EEG signal, wherein the step of obtaining representative numerical data is repeated a plurality of times with different time window and refractory time period values and the individual results are combined.

9. The method of detecting seizures as claimed in claim 5, wherein the step of carrying out at least one calculation on at least some of the representative numerical data includes determining the amplitude of the peak and trough in each data group with respect to a predetermined base level and associating the determined amplitude with its respective group.

10. The method of detecting seizures as claimed in claim 9, wherein the amplitude of at least one peak is determined relative to the two adjacent troughs, and the amplitude of at least one trough is determined relative to the two adjacent peaks.

11. The method of detecting seizures as claimed in claim 5, wherein the step of carrying out at least one calculation on at least some of the representative numerical data includes determining the time interval between at least one peak, trough, or intersection point from a first data group with its corresponding respective peak, trough, or intersection point from a subsequent data group and associating the determined time interval or intervals with one of the data groups.

12. The method of detecting seizures as claimed in claim 9, wherein for each pair of adjacent data groups, at least one comparison is made, wherein in the comparison, the determined amplitudes are compared to obtain said related numerical data in the form of a numerical indication of the similarity of the amplitude of the adjacent data groups or one or more of the respective determined time interval differences are compared to obtain said related numerical data in the form of a numerical indication of the similarity of the intervals of the adjacent data groups.

13. The method of detecting seizures as claimed in claim 12, wherein numerical values indicative of amplitude and interval difference are combined in predetermined ratios to provide said predetermined criteria.

14. The method of detecting seizures as claimed in claim 13, wherein the numerical values indicative of amplitude and interval difference are combined in a plurality of different ratios in order to produce multiple separate criteria as said predetermined criteria.

15. The method of detecting seizures as claimed in claim 13, wherein a determination that a seizure event has taken place is made only if the related data remains within the predetermined criteria for a predetermined number of adjacent data groups.

16. The method of detecting seizures as claimed in claim 8, wherein said related numerical data also includes data representative of the change in shape of the EEG signal as described by a predetermined number of serially adjacent data groups.

17. The method of detecting seizures as claimed in claim 5, wherein each point in said averaged EEG signal is shifted upwards by a predetermined amount prior to the step of comparing the EEG signal to the averaged EEG signal.

18. The method of detecting seizures as claimed in claim 9, wherein a seizure event will not be determined for times within the EEG signal where the amplitude or average amplitude of a predetermined number of serially adjacent peaks or a predetermined number of serially adjacent troughs is less than a predetermined threshold.

19. The method of detecting seizures as claimed in claim 1, wherein noise introduced into the EEG signal by at least one of external electrical or mechanical equipment is detected, and a seizure event will not be determined to have occurred during periods of time in which the noise exceeds a predetermined threshold.

20. The method of detecting seizures as claimed in claim 8, wherein one of the different time window and refractory time period value combinations detects noise added to the EEG signal by at least one of external electrical or mechanical equipment.

21. The method of detecting seizures as claimed in claim 1, wherein the EEG signal undergoes analog to digital conversion and is then band-pass filtered prior to said step of obtaining representative numerical data characterising the waveform.

22. The method of detecting seizures as claimed in claim 1, further comprising the step of:
comparing the shapes of adjacent portions of the EEG signal to obtain related numerical data indicative of the variability of the shape of the EEG signal from portion to portion,
wherein a seizure event will not be determined to have occurred for times within the EEG signal where the related numerical data indicative of the variability of the shape of the EEG signal does not meet predetermined variability criteria.

23. The method of detecting seizures as claimed in claim 22, wherein the related numerical data includes the linear coefficient of correlation between adjacent portions of the EEG signal.

24. The method of detecting seizures as claimed in claim 1, further comprising the step of:
analyzing the shape of at least one selected portion of the EEG signal to obtain related numerical data indicative of the shape of the at least one selected portion of the EEG signal,
wherein a seizure event will not be determined to have occurred for times within the EEG signal where the related numerical data indicative of the shape of the at least one selected portion of the EEG signal does not meet predetermined shape criteria.

25. The method of detecting seizures as claimed in claim 24, wherein the at least one portion of the EEG signal is between adjacent peaks in the EEG signal and the predetermined shape criteria include a requirement that each at least one portion of the EEG waveform must include a central dip in amplitude.

26. A non-transitory computer readable medium on which a computer program is stored, the computer program, when executed on a computer, enabling the computer to detect seizures in an electroencephalogram (EEG) signal by:
i) generating an EEG signal from a set of electrodes applied to an animal's cranium, obtaining representative numerical data from the EEG signal and characterising the waveform shape of the EEG signal at a plurality of times within the EEG signal, the representative numerical data obtained by comparing the EEG signal to an averaged EEG signal to locate intersection positions to determine the location of each peak or trough of the EEG signal and record the position of each trough, subsequent peak and two corresponding intersection points in respective data groups, wherein obtaining representative numerical data is carried out on the inverted version of the EEG signal, and the representative numerical data from both the EEG signal and inverted version of the EEG signal are combined;
ii) carrying out at least one calculation on at least some of the representative numerical data to produce related numerical data indicative of individual oscillations identified within the EEG signal;
iii) comparing the related numerical data indicative of at least two individual oscillations identified to a predetermined criteria; and
iv) determining that a seizure event has taken place at a particular time or times in the EEG signal if the related numerical data indicative of individual oscillations identified at said particular time or times in the EEG signal are within the predetermined criteria; wherein a computer is configured to perform the steps i)-iv) above.

27. A computer implemented device incorporating and implementing a non-transitory computer readable medium for detecting seizures in an electroencephalogram (EEG) signal, the device configured to:
i) generate an EEG signal from a set of electrodes applied to an animal's cranium and to obtain an inverted version of the EEG signal;
ii) obtain representative numerical data characterising the waveform shape of the EEG signal at a plurality of times within the EEG signal, the representative numerical data obtained by comparing the EEG signal to an averaged EEG signal to locate intersection positions to determine the location of each peak or trough of the EEG signal and record the position of each trough, subsequent peak and two corresponding intersection points in respective data groups, wherein obtaining representative numerical data is carried out on the inverted version of the EEG signal, and the representative numerical data from both the EEG signal and inverted version of the EEG signal are combined;

iii) carry out a calculation or calculations on at least some of the representative numerical data to produce related numerical data indicative of individual oscillations identified within the EEG signal;

iv) compare the related numerical data of at least two individual oscillations identified to a predetermined criteria; and v) determine that a seizure event has taken place at a particular time or times in the EEG signal if the related numerical data of individual oscillations identified at said particular time or times in the EEG signal are within the predetermined criteria; wherein a computer is configured to perform the steps i)-v) above.

28. The device for detecting seizures as claimed in claim 27, wherein the EEG signal comprises multiple separate channels, and the means for obtaining representative numerical data obtains representative numerical data on each channel individually, and the individual results produced by the means for determining that a seizure event has taken place are combined together.

29. The device for detecting seizures as claimed in claim 27, further comprising: means for analyzing the length of a period of time between adjacent positive determinations of a seizure event and means for determining that a seizure event has taken place within said period of time if said length of time is less than a predetermined minimum time value.

30. The device for detecting seizures as claimed in claim 27, wherein said means for obtaining representative numerical data determines the positions of local peaks and troughs within the EEG signal.

31. The device for detecting seizures as claimed in claim 30, wherein said means for obtaining representative numerical data:

a) averages or low-pass filters the EEG signal to obtain the averaged EEG signal, b) compares the EEG signal to the averaged EEG signal to locate intersection positions where the EEG signal intersects with the averaged EEG signal, c) for each pair of first and subsequent intersection points, determines the location of each peak or trough of the EEG signal and, for each pair of subsequent and its subsequent intersection point, determines the location of each trough or peak of the EEG signal, and d) records the position of each trough, subsequent peak and two corresponding intersection points in respective data groups.

32. The device for detecting seizures as claimed in claim 31, wherein a comparison is made between the amount of time between adjacent peaks and a predetermined refractory time period, and if the time between adjacent peaks is less than the refractory time period, the later occurring of the adjacent peaks is disregarded.

33. The device for detecting seizures as claimed in claim 32, wherein if a plurality of peaks of the EEG signal are recorded within said refractory time period, all but the maximum of those peaks are disregarded.

34. The device for detecting seizures as claimed in claim 32, wherein the averaged EEG signal is determined by a moving average calculation based upon a predetermined time window of the EEG signal, wherein the means for obtaining representative numerical data from the EEG signal obtains a plurality of sets of representative data, each with different time window and refractory time period values, and the individual sets are combined.

35. The device for detecting seizures as claimed in claim 27, wherein the means for obtaining representative numerical data obtains said numerical data from the EEG signal and also from the inverted version of the EEG signal, and the results are combined.

36. The device for detecting seizures as claimed in claim 31, wherein the means for carrying out a calculation or calculations on at least some of the representative numerical data determines the amplitude of the peak and trough in each data group with respect to a predetermined base level and associates the determined amplitude with its respective group.

37. The device for detecting seizures as claimed in claim 36, wherein the amplitude of at least one peak is determined relative to the two adjacent troughs, and the amplitude of at least one trough is determined relative to the two adjacent peaks.

38. The device for detecting seizures as claimed in claim 31, wherein the means for carrying out a calculation or calculations on at least some of the representative numerical data determines the time interval between at least one peak, trough, or intersection point from a first data group with its corresponding respective peak, trough, or intersection point from a subsequent data group and associates the determined time interval or intervals with one of the data groups.

39. The device for detecting seizures as claimed in claim 36, wherein for each pair of adjacent data groups, at least one comparison is made, wherein in the comparison, the determined amplitudes are compared to obtain said related numerical data in the form of a numerical indication of the similarity of the amplitude of the adjacent data groups or one or more of the respective determined time interval differences are compared to obtain said related numerical data in the form of a numerical indication of the similarity of the intervals of the adjacent data groups.

40. The device for detecting seizures as claimed in claim 39, wherein numerical values indicative of amplitude and interval difference are combined in predetermined ratios to provide said predetermined criteria.

41. The device for detecting seizures as claimed in claim 40, wherein the numerical values indicative of amplitude and interval difference are combined in a plurality of different ratios in order to produce multiple separate criteria as said predetermined criteria.

42. The device for detecting seizures as claimed in claim 40, wherein a determination is made that a seizure event has taken place only if the related data remains within the predetermined criteria for a predetermined number of adjacent data groups.

43. The device for detecting seizures as claimed in claim 31, wherein said related numerical data also includes data representative of the change in shape of the EEG signal as described by a predetermined number of serially adjacent data groups.

44. The device for detecting seizures as claimed in claim 31, wherein each point in said averaged EEG signal is shifted upwards by a predetermined amount prior to the step of comparing the EEG signal to the averaged EEG signal.

45. The device for detecting seizures as claimed in claim 36, wherein a seizure event will not be determined for times within the EEG signal where the amplitude or average amplitude of a predetermined number of serially adjacent peaks or a predetermined number of serially adjacent troughs is less than a predetermined threshold.

46. The device for detecting seizures as claimed in claim 27, wherein noise introduced into the EEG signal by at least one of external electrical or mechanical equipment is detected, and a seizure event will not be determined to have occurred during periods of time in which the noise exceeds a predetermined threshold.

47. The device for detecting seizures as claimed in claim 34, wherein one of the different time window and refractory time period value combinations detects noise added to the EEG signal by at least one of external electrical or mechanical equipment.

48. The device for detecting seizures as claimed in claim 1, wherein the EEG signal undergoes analog to digital conversion and is then band-pass filtered prior to said means for obtaining representative numerical data characterising the waveform.

49. The device for detecting seizures as claimed in claim 27, further comprising: means for comparing the shapes of adjacent portions of the EEG signal to obtain related numerical data indicative of the variability of the shape of the EEG signal from portion to portion, wherein a seizure event will not be determined to have occurred for times within the EEG signal where the related numerical data indicative of the variability of the shape of the EEG signal does not meet predetermined variability criteria.

50. The device for detecting seizures as claimed in claim 49, wherein the related numerical data includes the linear coefficient of correlation between adjacent portions of the EEG signal.

51. The device for detecting seizures as claimed in claim 27, further comprising: means for analyzing the shape of a selected portion or portions of the EEG signal to obtain related numerical data indicative of the shape of the selected portion or respective portions of the EEG signal, wherein a seizure event will not be determined to have occurred for times within the EEG signal where the related numerical data indicative of the shape of the selected portion or portions of the EEG signal does not meet predetermined shape criteria.

52. The device for detecting seizures as claimed in claim 51, wherein the portion of the EEG signal is between adjacent peaks in the EEG signal, and the predetermined shape criteria include a requirement that each portion of the EEG waveform must include a central dip in amplitude.

* * * * *